(12) United States Patent
Sama (10) Patent No.: US 11,707,618 B2
(45) Date of Patent: Jul. 25, 2023

(54) ORAL MUSCLE TRAINING

(71) Applicant: Signifier Medical Technologies Limited, Leicester (GB)

(72) Inventor: Anshul Sama, Nottinghamshire (GB)

(73) Assignee: Signifier Medical Technologies Limited, London (GB)

( * ) Notice: Subject to any disclaimer, the term of this patent is extended or adjusted under 35 U.S.C. 154(b) by 322 days.

(21) Appl. No.: 16/776,946

(22) Filed: Jan. 30, 2020

(65) Prior Publication Data

US 2020/0164205 A1 May 28, 2020

Related U.S. Application Data

(63) Continuation of application No. 16/207,725, filed on Dec. 3, 2018, now Pat. No. 10,596,366, which is a continuation of application No. 15/955,121, filed on Apr. 17, 2018, now Pat. No. 10,561,836, which is a continuation of application No. 15/643,765, filed on Jul. 7, 2017, now Pat. No. 10,058,701, which is a continuation of application No. 15/026,104, filed as
(Continued)

(30) Foreign Application Priority Data

Dec. 3, 2014 (GB) ..................................... 1421448

(51) Int. Cl.
*A61N 1/05* (2006.01)
*A61N 1/36* (2006.01)
*A61N 1/372* (2006.01)

(52) U.S. Cl.
CPC ......... *A61N 1/0548* (2013.01); *A61N 1/3601* (2013.01); *A61N 1/36146* (2013.01); *A61N 1/37235* (2013.01)

(58) Field of Classification Search
CPC .............................. A61N 1/0548; A61N 1/3601
USPC ............................................................ 607/42
See application file for complete search history.

(56) References Cited

U.S. PATENT DOCUMENTS

| | | | |
|---|---|---|---|
| 5,190,053 A | 3/1993 | Meer | |
| 5,265,624 A | 11/1993 | Bowman | |
| 5,284,161 A | 2/1994 | Karell | |
| (Continued) | | | |

FOREIGN PATENT DOCUMENTS

| | | |
|---|---|---|
| CN | 101590302 | 12/2009 |
| CN | 101596340 | 12/2009 |
| (Continued) | | |

OTHER PUBLICATIONS

Steier et al.; Continuous transcutaneous submental electrical stimulation in obstructive sleep apnea; Chest; 140(4); pp. 998-1007; Oct. 2011.

*Primary Examiner* — Catherine M Voorhees
*Assistant Examiner* — Roland Dinga
(74) *Attorney, Agent, or Firm* — Shay Glenn LLP (57) ABSTRACT

A trans mucosal neuromuscular electrical stimulation device including a mouthpiece, electrodes associated with the mouthpiece. The device and/or mouthpiece incorporates electrical circuitry operatively connecting to the electrodes to a power source and is configured to provide, in use, electrical stimulation to one or more palate and/or tongue muscles via the electrodes through the oral mucosa. The treatment regime, including the location of stimulation and the parameters used, is designed to increase resting muscle tone and/or muscle tone during sleep.

12 Claims, 3 Drawing Sheets

Related U.S. Application Data application No. PCT/GB2015/052984 on Oct. 12, 2015, now Pat. No. 9,833,613.

(56) References Cited

U.S. PATENT DOCUMENTS

| | | | |
|---|---|---|---|
| 5,490,520 A | 2/1996 | Schaefer et al. | |
| 6,212,435 B1 * | 4/2001 | Lattner | A61N 1/0548 607/42 |
| 8,744,589 B2 | 6/2014 | Bolea et al. | |
| 9,717,904 B2 | 8/2017 | Simon et al. | |
| 9,833,613 B2 | 12/2017 | Sama | |
| 10,058,701 B2 | 8/2018 | Sama | |
| 10,195,426 B2 | 2/2019 | Kent et al. | |
| 10,463,850 B2 | 11/2019 | Fisk et al. | |
| 10,561,836 B2 | 2/2020 | Sama | |
| 10,596,366 B2 | 3/2020 | Sama | |
| 10,646,319 B2 | 5/2020 | Johansson et al. | |
| 10,709,887 B2 | 7/2020 | Guarraia et al. | |
| 2003/0003422 A1 | 1/2003 | Pasquantonio et al. | |
| 2005/0038485 A1 | 2/2005 | Ludwig et al. | |
| 2007/0123950 A1 | 5/2007 | Ludlow et al. | |
| 2007/0173893 A1 | 7/2007 | Pitts | |
| 2009/0048647 A1 | 2/2009 | Tingey | |
| 2009/0210032 A1 | 8/2009 | Beiski et al. | |
| 2010/0087893 A1 | 4/2010 | Pasquet | |
| 2010/0087896 A1 | 4/2010 | McCreery | |
| 2010/0204747 A1 | 8/2010 | Lindquist et al. | |
| 2011/0112601 A1 | 5/2011 | Meadows | |
| 2011/0155143 A1 | 6/2011 | Shantha | |
| 2014/0093832 A1 | 4/2014 | Nemeh et al. | |
| 2014/0135868 A1 | 5/2014 | Bashyam | |
| 2014/0277323 A1 | 9/2014 | Tingey | |
| 2015/0093716 A1 | 4/2015 | Fulton, III | |
| 2015/0142120 A1 | 5/2015 | Papay | |
| 2015/0190630 A1 | 7/2015 | Kent et al. | |
| 2016/0106976 A1 | 4/2016 | Kucklick | |
| 2016/0158093 A1 | 6/2016 | Amblard et al. | |
| 2017/0143257 A1 | 5/2017 | Kent et al. | |
| 2017/0143259 A1 | 5/2017 | Kent et al. | |
| 2017/0143960 A1 | 5/2017 | Kent et al. | |
| 2017/0224987 A1 | 8/2017 | Kent | |
| 2018/0036531 A1 | 2/2018 | Schwarz et al. | |
| 2020/0121921 A1 | 4/2020 | Sama | |
| 2020/0121924 A1 | 4/2020 | Sama | |
| 2020/0121984 A1 | 4/2020 | Sama | |

FOREIGN PATENT DOCUMENTS

| | | |
|---|---|---|
| CN | 102548610 | 7/2012 |
| EP | 0122102 | 10/1984 |
| GB | 1038829 | 8/1966 |
| JP | 2000511087 | 8/2000 |
| JP | 2014 158607 | 9/2014 |
| JP | 2015093133 A | 5/2015 |
| RU | 2223798 | 2/2004 |
| RU | 2457006 | 7/2012 |
| TW | I615168 B | 2/2018 |
| WO | 1992/015364 | 9/1992 |
| WO | 1997018854 | 5/1997 |
| WO | 2000029063 | 5/2000 |
| WO | 2002/066111 | 1/2002 |
| WO | 2005072821 | 8/2005 |
| WO | WO2006/001644 A1 | 1/2006 |
| WO | 2008/100779 | 8/2008 |
| WO | 2009127947 | 10/2009 |
| WO | 2013144710 | 10/2013 |

* cited by examiner

ORAL MUSCLE TRAINING

CROSS-REFERENCE TO RELATED APPLICATIONS

This application is a continuation of U.S. patent application Ser. No. 16/207,725, filed Dec. 3, 2018, which is a continuation of U.S. patent application Ser. No. 15/955,121, filed Apr. 17, 2018, which is a continuation of U.S. patent application Ser. No. 15/643,765, filed Jul. 7, 2017, which is a continuation of U.S. patent application Ser. No. 15/026,104, filed Mar. 30, 2016, which is a National Phase filing of PCT/GB2015/052984, filed Oct. 12, 2015, which claims the priority of UK Patent Application 1421448.0, filed Dec. 3, 2014, all of which are incorporated herein by reference.

FIELD OF THE INVENTION

This invention relates generally to oral muscle training, particularly to oral muscle training devices, methods, systems and control software. More specifically, although not exclusively, this invention relates to the training of muscles in the mouth for the treatment of sleep disordered breathing.

BACKGROUND OF THE INVENTION

Snoring and sleep apnea are considered as part of a range of conditions often termed as sleep disordered breathing (SDB), with symptoms relating to disordered breathing patterns during sleep. SDBs are not only a nuisance, but they can also result in health problems, for example frequent waking from sleep, light sleeping, strain on the heart, low oxygen levels in the blood, headaches and fatigue.

The breathing passage of humans between the back of the nose and mouth, to the level of the larynx, is a collapsible tube. It has been observed that collapse of the breathing passage occurs at a positive airway pressure in individuals who snore and/or suffer from sleep apnea syndrome and at a negative airway pressure in individuals who do not.

In an effort to address this phenomenon, treatments have been developed which include using a continuous positive airway pressure device to keep the breathing passage open or wearing a mandibular advancement device to hold the jaw and tongue forward in order to increase the space at the back of the throat.

These devices can cause discomfort, they address the symptoms only temporarily, rather than addressing the underlying cause, and they must be used during sleep on an ongoing basis. As a result, users find it difficult to fall asleep and compliance is therefore low. It would therefore be desirable to provide a treatment that does not require the regular use of such devices during sleep and that addresses the underlying cause for the condition.

Recent research studies have shown that implanting electrical nerve stimulators into the tongue and diaphragm are effective in the treatment of obstructive sleep apnea. This involves intrusive surgery to implant sensors and electrodes on nerves in these areas. The device identifies an episode of obstruction using the sensors and stimulates the tongue nerve to cause contraction to relieve the obstructive event. As with pacemakers, this approach leads to maintenance and other complications, such as battery replacement, risks associated with electrical fields and issues related to external security detection devices. In addition, stimulation only occurs during an obstructive episode during sleep; it does not address the underlying cause of the condition.

SUMMARY OF THE INVENTION

It is therefore a first non-exclusive object of the invention to provide a treatment system, preferably to be used in an awake state, that provides a sustainable reduction in disordered breathing patterns during sleep. It is a further, more general object of the invention to provide a treatment system and device that is more effective in at least one respect than existing systems and devices for the treatment of SDBs.

Accordingly, a first aspect of the invention provides an electrical stimulation device for training one or more oral muscles, for example a trans mucosal neuromuscular electrical stimulation device, the device comprising a mouthpiece, electrode means associated with the mouthpiece and electrical circuitry operatively connected to the electrode means, wherein the device or electrical circuitry is configured to provide, in use, via the electrode means electrical stimulation to one or more oral muscles, e.g. tongue muscle and/or palate muscles, through the lining of the mouth, for example the oral mucosa, e.g. to increase resting muscle tone and/or muscle tone during sleep.

When a person is awake, the collapsible segment of the breathing passage is kept open due to the tone of the muscles that control this area. When a person is asleep, this muscle tone reduces significantly. Evidence has shown that this reduction of muscle tone is significantly greater in patients who suffer from obstructive sleep apnoea, less so in those who snore and notably less in individuals who suffer from neither of these disorders.

Research has demonstrated that increasing the pharyngeal muscle activity or tone reduces the collapsibility of the airway and the present invention is based on the realisation that electrical stimulation, particularly neuromuscular electrical stimulation, can be used to stimulate the muscles of the tongue and/or palate and/or the sensory nerves to improve muscle power and tone recovery.

The device or electrical circuitry is preferably configured to provide a current, for example an electric current or impulse current, such as a biphasic electric current or impulse current.

Another aspect of the invention provides an electrical stimulation device for training one or more oral muscles, for example a trans mucosal neuromuscular electrical stimulation device, the device comprising a mouthpiece, electrode means associated with the mouthpiece and electrical circuitry operatively connected to the electrode means, wherein the device or electrical circuitry is configured to provide, in use, via the electrode means a biphasic electric current, for example biphasic electric impulse current.

By providing a biphasic electric current, particularly a biphasic electric impulse current, tongue and/or palate muscles contributing to the collapsibility of the airway can be stimulated along with the sensory nerves to increase resting muscle tone and muscle tone during sleep.

The current is preferably a biphasic symmetrical current, but it may additionally or alternatively be a biphasic asymmetrical current that may either be balanced or unbalanced. The device or electrical circuitry may be configured to provide, in use, via the electrode means an electric current with a frequency of between 5 and 150 Hz.

Another aspect of the invention provides an electrical stimulation device for training one or more oral muscles, for example a trans mucosal neuromuscular electrical stimulation device, the device comprising a mouthpiece, electrode means associated with the mouthpiece and electrical circuitry operatively connected to the electrode means, wherein the device or electrical circuitry is configured to provide, in use, via the electrode means an electric current with a frequency of between 5 and 150Hz.

The electric current may comprise a frequency of between 10 and 140 Hz, for example between 15 and 130 Hz, preferably between 20 and 120 Hz. Preferably, the electric current comprises a frequency of between 20 and 50 Hz and/or between 50 and 120 Hz.

The device or electrical circuitry may be configured to provide two or more currents, for example a first current and/or a second current, which second current may be different from and/or configurable or settable independently from the first current. At least one, e.g. both, of the first and/or second current may comprise a biphasic current, each of which is preferably symmetrical, but may be asymmetrical and either balanced or unbalanced. At least one of the first and/or second current may comprise a frequency of between 5 and 150 Hz, for example between 10 and 140 Hz, e.g. between 15 and 130 Hz, preferably between 20 and 120 Hz. In some embodiments, one or the currents may comprise a frequency of between 20 and 50 Hz and/or the other current may comprise a frequency of between 50 and 120 Hz.

The inventors believe that the application of an electric current in one or each of these two frequency ranges is particularly suited to targeting palate and tongue muscles contributing to the collapsibility of the airway.

The device or electrical circuitry may be configured to provide, in use, the or at least one or each electrical current to one or more oral muscles, such as palate and/or tongue muscles, for example through the lining of the mouth, e.g. the oral mucosa, such as to increase resting muscle tone and/or muscle tone during sleep. In some embodiments, the device is configured to provide, in use, the electrical current, e.g. the first electrical current, to one or more palate muscles. Additionally or alternatively, the device may be configured to provide, in use, the electrical current, e.g. the second electrical current, to one or more tongue muscles, e.g. via the dorsal tongue surface. Additionally or alternatively, the device may be configured to provide, in use, the electrical current, e.g. the first or second electrical current, to one or more tongue muscles via the underside of the tongue.

In embodiments, the mouthpiece may comprise one or more arms and/or one or more appendages or flanges which may extend from the one or more arms, e.g. for contacting one or more oral muscles. At least one arm and/or at least one appendage or flange may be flat or planar, for example with major surfaces. Optionally, the mouthpiece may comprise a pair of arms each of which may comprise one or more appendages or flanges. In some embodiments, the mouthpiece comprise a pair of arms that may extend at least partially alongside each other and/or at an angle relative to one another and/or parallel to each other. For example, the mouthpiece may comprise a pair of arms joined together at one end and diverging from one another, for example in a substantially V-shape or U-shape or horseshoe shape.

The one or more appendages or flanges may extend inwardly of the pair of arms, e.g. from one arm and toward the other arm. In some embodiments, each arm comprises at least one appendage or flange, for example opposite one another and/or extending toward one another. In embodiments, each arm comprises two or more appendages or flanges, for example an appendage or flange extending from a free end of each arm and/or an appendage or flange extending from an intermediate portion of each arm.

At least one appendage or flange may be curved, e.g. a flat curved shape or member, and/or extend upwardly or downwardly or out of the plane of the mouthpiece or at least one arm thereof. At least one appendage or flange may be shaped to cooperate or approximate or accommodate a tongue surface, for example a dorsal tongue surface or a sublingual tongue surface. In embodiments, the mouthpiece comprises at least one appendage or flange that is shaped to cooperate or approximate or accommodate a dorsal tongue surface and at least one appendage or flange that is shaped to cooperate or approximate or accommodate a sublingual tongue surface. In embodiments having a pair of arms, each arm may comprise an appendage or flange shaped to cooperate or approximate or accommodate a dorsal tongue surface and an appendage or flange that is shaped to cooperate or approximate or accommodate a sublingual tongue surface.

At least one of the appendages or flanges may comprise one or more electrodes or series thereof. At least one electrode or series of electrodes may be adjacent and/or associated with and/or exposed at a surface, e.g. a major surface, of the at least one appendage or flange. In embodiments, at least one of the appendages or flanges comprises electrodes associated with each of its major surfaces. The electrodes associated with one of the major surfaces may be isolated and/or controllable independently from another or the other major surface thereof. Additionally or alternatively, the electrodes of or associated with one appendage or flange may be isolated and/or controllable independently from at least one other appendage or flange.

In embodiments, the mouthpiece may comprise a pair of arms joined together at one end and diverging from one another to provide a substantially horseshoe shape with one or more flanges extending inwardly from at least one arm, the or each flange comprising electrode means. The mouthpiece may comprise a pair of flanges each extending inwardly from a respective arm, which flanges are shaped to accommodate a dorsal tongue surface. The mouthpiece may comprises a pair of flanges each extending inwardly from a respective arm, which flanges are shaped to accommodate a sublingual tongue surface. Each of the pair of flanges may be shaped to accommodate a dorsal tongue surface extends from at or adjacent a free end of the arm and/or each of the pair of flanges may be shaped to accommodate a sublingual tongue surface extends from an intermediate portion of the arm.

Another aspect of the invention provides an electrical stimulation device for training one or more oral muscles, for example a trans mucosal neuromuscular electrical stimulation device, the device comprising a mouthpiece, electrode means associated with the mouthpiece and electrical circuitry operatively connected to the electrode means, wherein the mouthpiece comprises a pair of arms joined together at one end and diverging from one another with one or more flanges extending inwardly from at least one arm, the or each flange including at least part of the electrode means associated therewith for providing electrical stimulation to one or more oral muscles.

Yet another aspect of the invention provides an electrical stimulation mouthpiece for training one or more oral muscles, for example a trans mucosal neuromuscular electrical stimulation mouthpiece, the mouthpiece comprising a pair of arms joined together at one end and diverging from one another with one or more flanges extending inwardly from at least one arm, wherein the or each flange includes electrode means associated therewith for providing electrical stimulation to one or more oral muscles.

The mouthpiece may comprise a gripping base, which may comprise an enlarged end, e.g. an enlarged free end, which may be connected or secured to, e.g. formed integrally with, the mouthpiece or a body or one or more or each arm thereof, for example by a necked portion.

The electrode means preferably comprises at least one anode and at least one cathode, for example two or more anodes and/or two or more cathodes, e.g. a plurality of anodes and a plurality of cathodes. At least part of the electrode means, for example one or more or each or all of the electrodes, may be mounted to or on or within and/or at least partially housed or contained within the mouthpiece. In some embodiments, the mouthpiece comprises a shield or shield means, for example on one side of the electrode means, e.g. for inhibiting or preventing the electrical stimulation or current from being applied or provided by or at or from one side of the mouthpiece. Suitable materials for the shield or shield means will be apparent to those skilled in the art.

In embodiments, the electrode means is configured or operable to provide or apply, e.g. selectively, the electrical stimulation or current at or from at least one or each or both sides, for example by including the or a shielding means or shield between a first set or series of electrode means or electrodes and a second set or series of electrode means or electrodes. In some embodiments, the first electrical current is provided or applied at or from a first side, e.g. major side, of the mouthpiece and/or by the first set or series of electrode means or electrodes. Additionally or alternatively, the second electrical current may be provided or applied at or from a second side, e.g. major side, of the mouthpiece and/or by the second set or series of electrode means or electrodes. In other embodiments, the first and second electrical currents may be provided or applied from at least one or each or both sides.

The mouthpiece may be insertable into the mouth and held in place, e.g. manually. The mouthpiece may be at least partially flattened and/or substantially flat and/or paddle-shaped, for example with at least one flat and/or major surface, preferably two flat major surfaces. In some embodiments, the device may include a handle to which the mouthpiece may be connected or mounted or attached, for example rigidly and/or releasably, e.g. to enable the mouthpiece to be inserted and/or held, in use, within one or more locations or positions and/or orientations within the mouth. In some embodiments, the mouthpiece is free of any mounting means for mounting or securing it to or in or within the mouth of a user.

In embodiments, the mouthpiece may include a mounting means. The mounting means may be for mounting the mouthpiece to an upper part or portion of the mouth, for example such that he mouthpiece or the or a first side or surface thereof is or may be in contact with and/or adjacent one or more palate muscles and/or the roof of the mouth and/or the mouthpiece or the or a second side or surface thereof is or may be in contact with and/or adjacent one or more tongue muscles, for example a dorsal tongue surface. Additionally or alternatively, the mounting means may be for mounting the mouthpiece to a lower part or portion of the mouth, for example such that the mouthpiece or the or a first side or surface thereof is or may be in contact with and/or adjacent one or more tongue muscles, for example a sublingual tongue surface. In embodiments, the device comprises a first mouthpiece with mounting means for mounting it to an upper part or portion of the mouth and a second mouthpiece for mounting it to a lower part or portion of the mouth.

The device or handle may comprise an input means or activator, which may include one or more input devices, buttons and/or push buttons and/or switches and/or dials or the like, e.g. for enabling or activating or initiating the electrical stimulation or current. The device or handle may comprise a power source and/or a cable connectable to a power source. In some embodiments, the device comprises a main body that includes or incorporates or provides the handle and/or which includes or houses the power source, which may comprise a rechargeable power source or one or more batteries that may be rechargeable, and/or which can either include the cable or be operatively, e.g. inductively, connectable to a charging station that includes or incorporates the cable, for example to enable the power source to be recharged. The device may include the charging station.

In some embodiments, the device comprises an adjustment means or adjuster, e.g. a frequency adjustment means or adjuster, for adjusting the frequency of the current or of the first and/or second currents, for example a respective first and second current frequency adjustment means or adjuster for adjusting the frequency of the current, e.g. between one of the aforementioned ranges. In embodiments, the adjustment means or adjuster is a step-wise adjustment means or adjuster and/or is configured to enable a user to select from one of two or more, e.g. three, four or five, predetermined frequency settings. The device may be operable or configured to provide the first and second currents simultaneously and/or concurrently and/or in parallel. Additionally or alternatively, the device may be operable or configured to provide the first and second currents in series and/or in sequence and/or in succession.

The current or at least one, e.g. both, of the first and/or second current may comprise an impulse current. The pulse duration of the or each impulse current may be between 50 and 1000 µs, for example between 100 and 900 µs, e.g. between 150 and 800 µs, preferably between 200 and 700 µs. Preferably, the or a further adjustment means or adjuster, e.g. an pulse duration adjustment means or adjuster, of the device is provided for adjusting the pulse duration, for example between one of the aforementioned ranges.

The electrical stimulation or current or first and/or second currents may comprise an intensity or current amplitude, which is preferably selected or selectable to provide maximum contraction of the muscles being treated. By way of example, the intensity or amplitude may comprise approximately 10 mA, for example between 1 and 100 mA, such as between 5 and 50 mA, for example between 5 and 15 mA or between 7 and 25 mA, e.g. between 8 and 12 mA. The or a further adjustment means or adjuster, e.g. an intensity or amplitude adjustment means or adjuster, may be provided for adjusting the intensity or amplitude, for example from 0 to 500 mA or from 0 to 250 mA or from 0 to 200 mA or from 0 to 150 mA or from 0 to 100 mA.

In some embodiments, the device is configured or programmed to provide the electrical stimulation or electric current or the first and/or second electric current for a predetermined period, which may comprise between 1 minute and 1 hour, for example between 5 and 30 minutes, preferably between 10 and 20 minutes. The or a further adjustment means or adjuster, e.g. a treatment duration adjustment means or adjuster, may be provided for adjusting the treatment duration, for example from 0 to 10 hours or from 0 to 5 hours or from 0 to 1 hour or from 0 to 30 minutes.

The device may comprise a control means, which may be programmed or programmable, for example to control one or more features of the electrical stimulation or current or currents, for example according to a predetermined treatment regime. The control means may comprise a control system and/or a controller and/or may comprise or be at least partially comprised in the electrical circuitry. The control means may comprise at least part of the adjustment means or adjuster, e.g. one or more of the frequency and/or pulse duration and/or intensity and/or amplitude and/or treatment duration adjustment means or adjusters.

In some embodiments, the input means may be for or configured or operable to control and/or adjust one or more features of the electrical stimulation or electric current or the first and/or second electric current, for example the frequency and/or pulse duration and/or intensity and/or amplitude and/or treatment duration. Additionally or alternatively the device or input means may comprise an interface or connection means such as a connector or receptacle for connecting the device or control means to another device, such as a personal computer or a handheld device, which may be operable to program and/or control and/or adjust one or more of the aforementioned features.

The device or control means or adjustment means may be configured or programmed to control one or more features of the electrical stimulation or electric current or the first and/or second electric current, for example in a predetermined manner and/or according to a predetermined treatment regime. The device or control means may be operable or programmable to create and/or alter the predetermined treatment regime, for example by a device to which the electrical stimulation device is connected, e.g. via the input means.

Another aspect of the invention provides a computer program element comprising computer readable program code means for causing a processor to execute a procedure to implement a method or treatment regime comprising providing electrical stimulation to one or more oral muscles, e.g. palate and/or tongue muscles, through the lining of the mouth, for example the oral mucosa, e.g. to increase resting muscle tone and/or muscle tone during sleep.

Another aspect of the invention provides a method or treatment regime, e.g.

for training one or more oral muscles such as by trans mucosal neuromuscular electrical stimulation, the method comprising providing or applying electrical stimulation to one or more oral muscles, e.g. palate and/or tongue muscles, through the lining of the mouth, for example the oral mucosa, e.g. to increase resting muscle tone and/or muscle tone during sleep.

For the avoidance of doubt, any of the features described herein apply equally to any aspect of the invention.

The method or treatment regime may comprise providing or applying a current, for example an electric current or impulse current, such as a biphasic electric current or impulse current, e.g. to the one or more oral muscles.

Another aspect of the invention provides a method or treatment regime, e.g. for training one or more oral muscles such as by trans mucosal neuromuscular electrical stimulation, the method comprising providing or applying, e.g. via electrode means, a biphasic electric current, for example biphasic electric impulse current, to one or more oral muscles, e.g. palate and/or tongue muscles, through the lining of the mouth, for example the oral mucosa.

The method or treatment regime may comprise providing or applying a first current and/or a second current, which second current may be different from the first current. The current or at least one, e.g. both, of the first and/or second current may comprise an alternating current. The or at least one of the or each current may comprise a frequency of between 5 and 150 Hz, for example between 10 and 140 Hz, e.g. between 15 and 130 Hz, preferably between 20 and 120 Hz, more preferably between 20 and 50 Hz and/or between 50 and 120 Hz. In some embodiments, the first current comprises a frequency of between 20 and 50 Hz and/or the second current comprises a frequency of between 50 and 120 Hz.

In embodiments, phases of the biphasic current, or the first and second currents, may be applied simultaneously and/or concurrently. In some embodiments, phases of the biphasic current, or the first and second currents, may be applied in series and/or in sequence and/or in succession.

The current or at least one, e.g. both, of the first and/or second current may comprise an impulse current. The pulse duration of the or each impulse current may be between 50 and 1000 µs, for example between 100 and 900 µs, e.g. between 150 and 800 µs, preferably between 200 and 700 µs.

The electrical stimulation or current or first and/or second currents may comprise an intensity or current amplitude, which is preferably selected or selectable to provide maximum contraction of the muscles being treated. By way of example, the intensity or amplitude may comprise approximately 10 mA, for example between 1 and 100 mA, such as between 5 and 50 mA, for example between 5 and 15 mA or between 7 and 25 mA, e.g. between 8 and 12 mA.

The method or treatment regime may comprise providing or applying the electrical stimulation or electric current or the first and/or second electric current for a predetermined period, which may comprise between 1 minute and 1 hour, for example between 5 and 30 minutes, preferably between 10 and 20 minutes.

In some embodiments, the method or treatment regime may comprise providing or applying the electrical stimulation or electric current or the first and/or second electric current for a first predetermined period to a first muscle or group of muscles and/or to an upper or dorsal surface of the tongue. The first muscle or group of muscles may include one or more palate and/or tongue muscles, e.g. one or more of the intrinsic surface muscles, the uvular muscle, the levator veli palatini muscle and the palatopharyngeus muscle.

Additionally or alternatively, the method or treatment regime may comprise providing or applying the electrical stimulation or electric current or the first and/or second electric current for a second predetermined period to a second muscle or group of muscles and/or to the underside of the tongue, e.g. sublingually. The second muscle or group of muscles may include one or more palate and/or tongue muscles, one or more of which may be different from the first muscle or group of muscles e.g. the genioglossus muscle. By way of example, the first predetermined period may comprise between five and thirty minutes, for example five or ten or fifteen or twenty or thirty minutes and/or the second predetermined period may comprise between five and thirty minutes, for example five or ten or fifteen or twenty or thirty minutes.

Additionally or alternatively, the method or treatment regime comprises carrying out one or more of the aforementioned steps at predetermined intervals, which may comprise between one and ten times per day or any number therebetween, for example twice per day. Additionally or alternatively, the method or treatment regime comprises carrying out one or more of the aforementioned steps over a predetermined treatment period, which may comprise between one and twelve weeks, for example between two and ten weeks, e.g. between five and eight weeks, such as six weeks.

The method or treatment regime may comprise adjusting one or more features of the electrical stimulation or electric current or the first and/or second electric current, for example the frequency and/or pulse duration and/or intensity and/or amplitude and/or treatment duration. The adjustment may be carried out using an input means, such as one or more push buttons and/or dials or the like or via an interface or connection means such as a connector or receptacle by a device, such as a personal computer or a handheld device.

In some embodiments, the method or treatment regime comprises a first, e.g. treatment, period, for example during which the electrical stimulation or electric current or the first and/or second electric current is or are provided or applied, e.g. to build resting muscle tone and/or muscle tone during sleep. The method or treatment regime may also comprise a second, e.g. maintenance, period, for example during which one or more features of the electrical stimulation or electric current or the first and/or second electric current is adjusted or changed, e.g. with respect to the first period, e.g. to maintain resting muscle tone and/or muscle tone during sleep. The first period may comprise a first regime and/or the second period may comprise a second regime, e.g. different from the first regime.

In an exemplary embodiment, the method or treatment regime comprises providing or applying electrical stimulation to the one or more oral muscles for 10 to 20 minutes, twice per day for six weeks, for example to build resting muscle tone and/or muscle tone during sleep. Additionally or alternatively, the method or treatment regime may comprise providing or applying electrical stimulation to the one or more oral muscles for 10 to 20 minutes, once per day on an ongoing basis, for example to maintain resting muscle tone and/or muscle tone during sleep.

Another aspect of the invention provides a method or treatment regime, e.g. for training one or more oral muscles such as by sensory stimulation, the method comprising providing or applying a vibratory stimulation to one or more oral muscles, e.g. palate and/or tongue muscles. The method may further comprise any one or more features of the method described above.

A further aspect of the invention provides a computer program element comprising computer readable program code means for causing a processor to execute a procedure to implement the aforementioned method or treatment regime. A yet further aspect of the invention provides the computer program element embodied on a computer readable medium.

A yet further aspect of the invention provides a computer readable medium having a program stored thereon, where the program is arranged to make a computer execute a procedure to implement the aforementioned method or treatment regime.

A yet further aspect of the invention provides a control means or control system or controller comprising the aforementioned computer program element or computer readable medium or for controlling a treatment regime to train one or more oral muscles, such as by trans mucosal neuromuscular electrical stimulation, for example for controlling the method described above.

Within the scope of this application it is expressly envisaged that the various aspects, embodiments, examples and alternatives set out in the preceding paragraphs, in the claims and/or in the following description and drawings, and in particular the individual features thereof, may be taken independently or in any combination. Features described in connection with one aspect or embodiment of the invention are applicable to all aspects or embodiments, unless such features are incompatible.

BRIEF DESCRIPTION OF THE DRAWINGS

Embodiments of the invention will now be described by way of example only with reference to the accompanying drawings in which.

DETAILED DESCRIPTION OF ILLUSTRATIVE EMBODIMENTS

Referring now to FIGS. 1 to 4, there is shown an electrical stimulation device 1 including a main body 2, a mouthpiece 3 and a charging station 4. The main body 2 serves as a handle, is substantially cylindrical in this embodiment and includes a first, upper end 20 with a male connector 21 having a projection 22 on each of its side to provide a bayonet fitting and an electrical socket 23 for receiving an electrical connector (not shown) of the mouthpiece 3. On its front surface, the main body 2 also includes an ON/OFF button 2a, four dials 24, 25, 26, 27, a USB port 28 and a second, lower end 29 with a receptacle (not shown) for receiving a projection 41 of the charging station 4.

Figure 1:
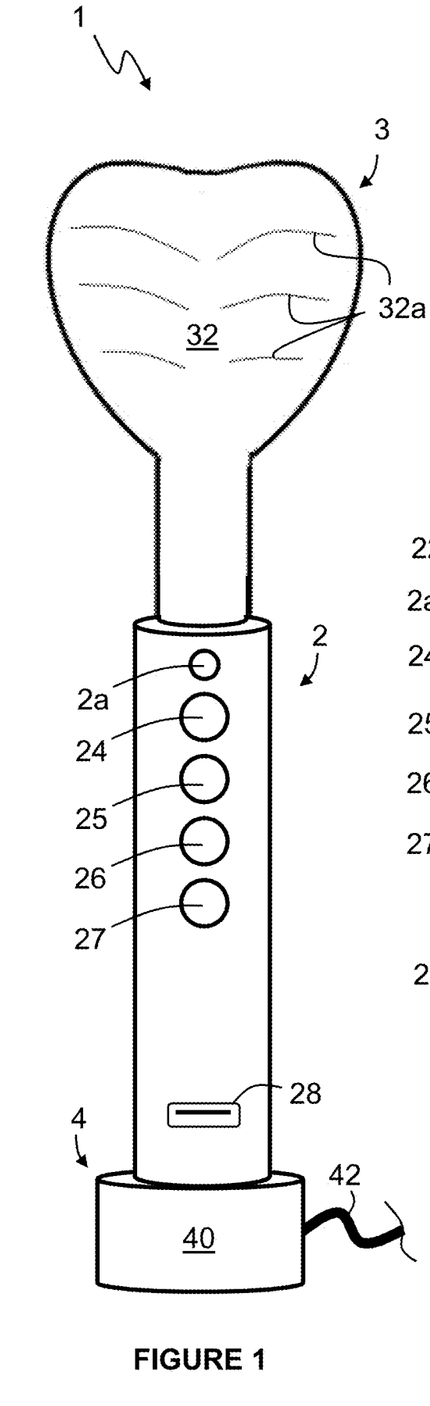
FIG. 1 is a perspective view of an electrical stimulation device according to an embodiment of the invention.
Figures 2, 3, 4:
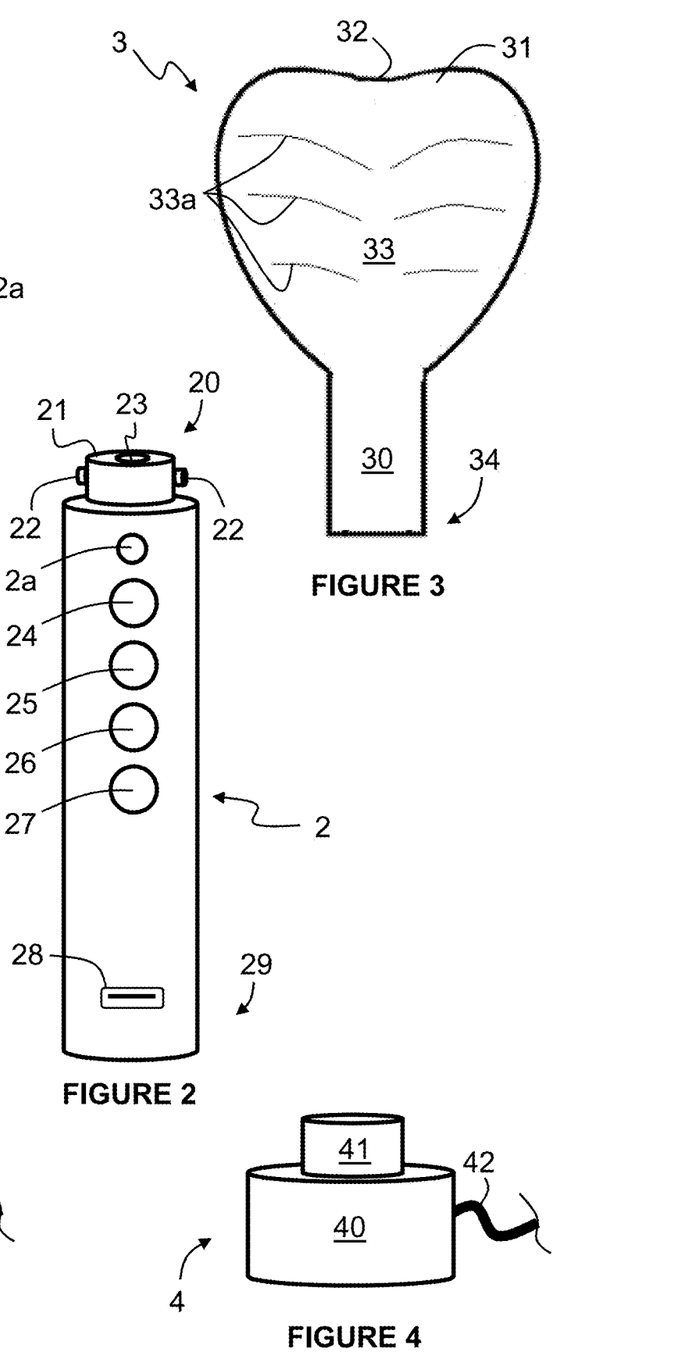
FIG. 2 is a perspective view of the main body of the device of FIG. 1.
FIG. 3 is a perspective view of the mouthpiece of the device of FIG. 1.
FIG. 4 is a perspective view of the charging station of the device of FIG. 1.

The main body 2 also contains batteries (not shown) and electrical circuitry including inverters for converting the direct current of the batteries into two separate symmetrical biphasic currents. The first dial 24 is operable to adjust the current amplitude of a first biphasic current from 0 to 100 mA. The second dial 25 is operable to adjust the current amplitude of a second biphasic current from 0 to 100 mA. The third dial 26 is operable to adjust the duration of the period during which the first biphasic current is supplied from 1 to 30 minutes. The fourth dial 27 is operable to adjust the duration of the period during which the second biphasic current is supplied from 1 to 30 minutes.

The USB port 28 is configured to enable the device 1 to be connected to a personal computer (not shown) to program one or more characteristics of the first and second biphasic currents independently. In this embodiment, the frequency of the first biphasic current is set at a value between 20 and 50 Hz, the second biphasic current is set at a value between 50 and 120 Hz and the pulse duration of each biphasic current is set at a value between 200 and 700 µs. The personal computer (not shown) may also incorporate control software operable to override the dials 24, 25, 26, 27. The software may be programmed to apply biphasic currents having predetermined characteristics independent from one another, such as amplitudes, frequencies and pulse durations and for a predetermined period of time. It is further envisaged that the device 1 could incorporate a memory on which is stored such predetermined characteristics, which may be modified by connecting a personal computer (not shown) to the device 1 via the USB port 28. In such embodiments, the dials may be omitted or configured to adjust the aforementioned characteristics from their pre-programmed values. In some embodiments, it is envisaged that more or less functionality is provided by manual dials, buttons and the like.

The mouthpiece 3 includes a cylindrical base 30 and a substantially flat, paddle-shaped contact portion 31 formed integrally with an upper end of the base 30 and having first and second major surfaces 32, 33. The base 30 includes a receptacle (not shown) at its lower end 34 with an electrical connector (not shown) for receipt within the electrical socket 23 of the main body 2. The mouthpiece 3 also includes electrical circuitry (not shown) feeding a respective series of electrodes 32a, 33a beneath each of the major surfaces 32, 33. The electrode series 32a, 33a are electrically isolated from one another by a shielding material. The electrical circuitry (not shown) of the mouthpiece 3 is operatively connected, in use, to the electrical circuitry (not shown) of the main body 2 such that a first series of the electrodes 32a delivers the first biphasic current and a second series of electrodes 33a delivers the second biphasic current.

In this embodiment, the mouthpiece 3 is provided as a separate component from the main body 2 and is configured such that it may be easily cleaned between sessions. However, in alternative embodiments, the mouthpiece 3 may be formed integrally with the main body 2. In yet further embodiments, the mouthpiece 3 may incorporate mounting means for mounting it to an upper and/or lower part of a user's mouth in a similar manner to a retainer. In such embodiments, the device 1 could include a pair of mouthpieces 3 each incorporating a mounting means, wherein a first mouthpiece 3 is adapted to be mounted to an upper part of the user's mouth and a second mouthpiece 3 is adapted to be mounted to a lower part of the user's mouth. The first mouthpiece 3 could incorporate two series of electrodes 32a, 33a to contact the roof of the user's mouth and stimulate one or more palate muscles on one side and to contact the dorsal surface of the tongue and stimulate one or more tongue muscles on its other side. The second mouthpiece 3 could incorporate a single series of electrodes 32a to stimulate the sublingual muscles. The or each mouthpiece 3 may include the power source and, for example, a wireless communication means, such as a Bluetooth communication means, that communicates with the personal computer (not shown).

The charging station 4 has a cylindrical base 40 with a cylindrical projection 41 and an electrical cable 42 for connecting the charging station 4 to a source of mains electricity. The projection 41 in this embodiment incorporates an inductive coupling and the station 4 includes electrical circuitry connected to the electrical mains cable 42 for supplying electricity to the inductive coupling to inductively charge the batteries (not shown) in the main body 2.

Figure 5:
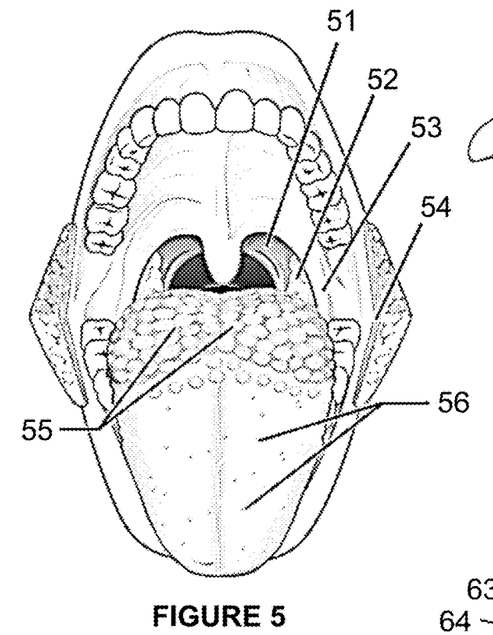
FIG. 5 is a schematic of a human mouth showing the palatoglossus and surface of the tongue.
Figure 6:
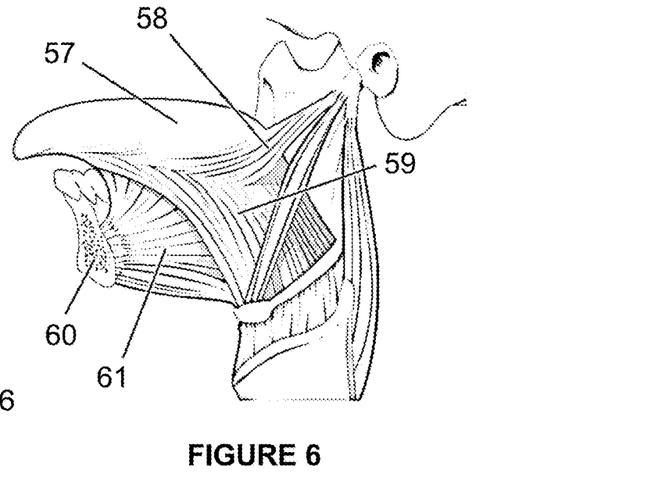
FIG. 6 is a schematic illustrating the extrinsic tongue muscles of a human tongue.
Figure 7:
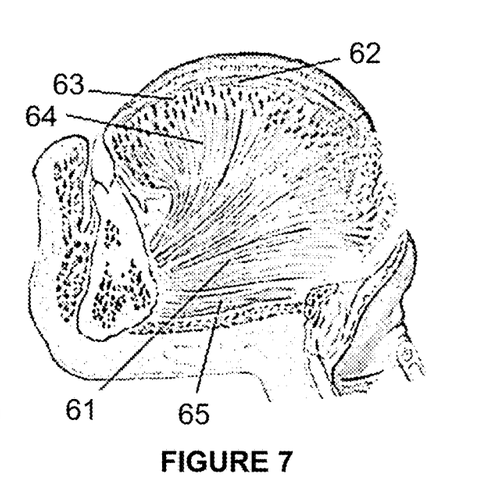
FIG. 7 is a schematic illustrating the intrinsic tongue muscles of a human tongue.

Turning now to FIGS. 5 to 9, there is shown various tongue and palate muscles. Features of the mouth shown in FIGS. 5 to 7 illustrate more clearly the tongue muscles, wherein there is shown the pharyngopalatine arch 51, palatine tonsil 52, palatoglossus 53, buccinator 54, valate papillae 55, fungiform papillae 56, dorsal tongue surface 57, styloglossus 58, hyoglossus 59, mandible bone 60, genioglossus 61, longitudinal, transverse and vertical intrinsic muscles 62, 63, 64 and geniohydoid 65.

It is well established that the tone of the genioglossus muscle 61 most affects the collapsibility of the tongue as it is the biggest of the extrinsic muscle and responsible for pulling the tongue forward and increasing the airway opening in the throat. The tone of intrinsic surface muscles, such as the longitudinal and transverse intrinsic muscles 62, 63, also contribute to the reduction of the collapsibility of the airway.

Figure 8:
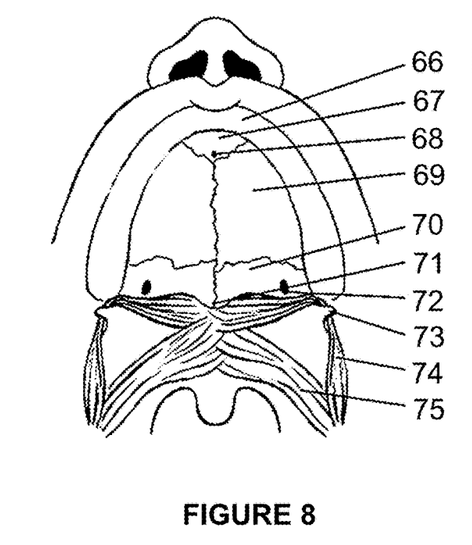
FIG. 8 is another schematic of a human mouth showing the muscles of the palate.
Figure 9:
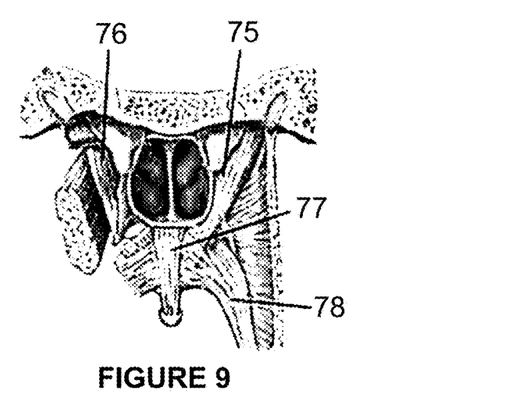
FIG. 9 is a schematic illustrating further muscles of the palate.

Features of the mouth shown in FIGS. 8 and 9 illustrate more clearly the palate muscles, wherein there is shown the dental arch 66, premaxilla 67, incisive foramen 68, palatine process of maxilla 69, palatine bone 70, posterior nasal spine 71, palatine foramen 72, hamulus 73, tensor palatini muscle 74, levator veli palatini muscle 75, tensor veli palatini muscle 76, uvular muscle 77 and palatopharyngeus muscle 78.

To a varying degree, the constrictor and dilator muscles of the palate also contribute to snoring and sleep apnoea. The aim of the treatment is to dilate the throat, hence electrical stimulation is directed at the dilatory palate muscles in the midline, such as the uvular muscle 77, the levator veli palatini muscle 75 and the palatopharyngeus muscle 78.

In use, the mouthpiece 3 is applied to the dorsal tongue surface 57 and the aforementioned palate muscles and two biphasic currents are applied, each of which is configured with a first set of parameters including intensity, frequency and pulse duration. These biphasic currents are transmitted through the lining of the mouth, the oral mucosa, to stimulate the intrinsic surface muscles 62, 63, the uvular muscle 77, the levator veli palatini muscle 75 and the palatopharyngeus muscle 78. The parameters are selected to provide maximal contraction of these muscles in the user and the treatment is carried out for a period of 20 minutes.

The intensity, frequency and pulse duration are then adjusted and the mouthpiece 3 is applied to the underside of the tongue. The two biphasic currents, now having a second set of parameters, are applied and transmitted trans mucosally to stimulate the genioglossus muscle 61. The second set of parameters are selected to provide maximal contraction of the user's genioglossus muscle 61 and the treatment is carried out for a period of 20 minutes.

The application of biphasic currents according to the parameters described above stimulate the aforementioned skeletal muscles. It is also believed that the application of this biphasic current to these skeletal muscles creates a further, sensory function, such as a vibratory sensation. Whilst not wishing to be bound by any theory, it is believed that this electrical and vibratory stimulation of the nerves provides feed back to the brain which further enhances the improvement in muscle tone. Specifically, it is believed that the effectiveness of this treatment is enhanced by multisensory integration within the nervous system.

By way of example, a treatment regime could involve a six week induction period during which each of the aforementioned muscle groups are stimulated for a period of 10 to 20 minutes, twice daily. The treatment regime, which is designed to build muscle tone, could then be followed by an ongoing maintenance regime involving 10 to 20 minute sessions once per day.

Figure 10:
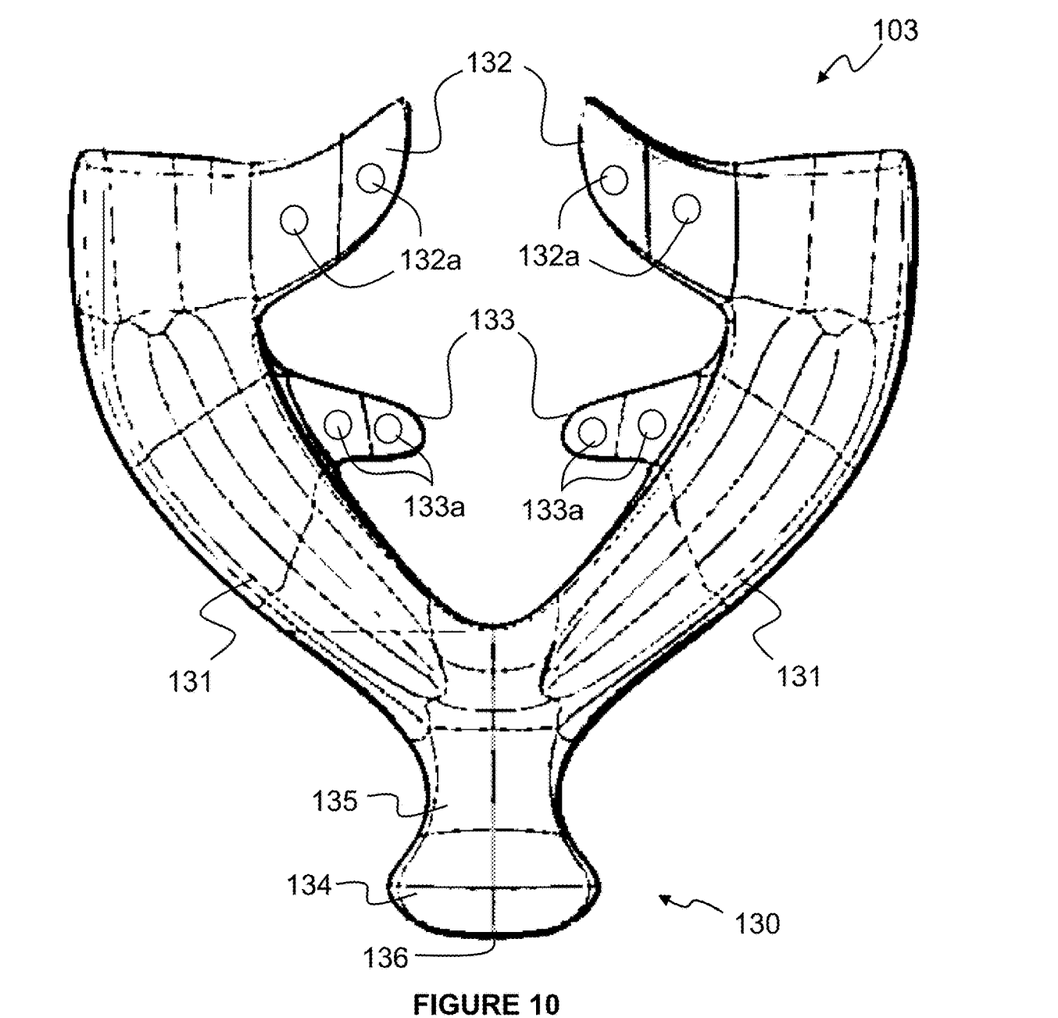
FIG. 10 is a top view of the mouthpiece of an electrical stimulation device according to a second embodiment of the invention.
Figure 11:
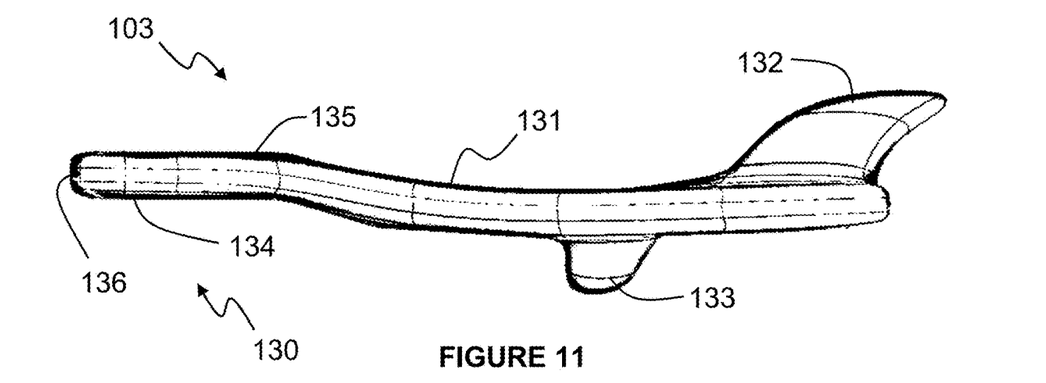
FIG. 11 is a side view of the mouthpiece of FIG. 10.

Referring now to FIGS. 10 and 11, there is shown a mouthpiece 103 according to a second embodiment similar to the first embodiment, wherein like references depict like features with a prefix 1. The mouthpiece 103 according to this embodiment includes a gripping base 130 and a pair of curved arms 131 formed integrally with one end of the base 130 to form a horseshoe shape. Each of the arms has first and second contact flanges 132, 133 within which is embedded electrodes (not shown).

The first contact flanges 132 extend inwardly toward one another from the free end of a respective one of the arms 131 and upwardly to form a curved shape for accommodating the dorsal tongue surface 57 of a tongue of a patient (not shown). The second contact flanges 133 extend inwardly toward one another from an intermediate part of a respective one of the arms 131 and downwardly to form a curved shape for accommodating the sublingual tongue surface.

The base 130 includes an enlarged end 134 joined to the arms 131 by a necked portion 135. The end surface of the enlarged end 134 includes an electrical connector 136 for connection with a source of power (not shown). The connector 136 may comprise a USB, microUSB or any other suitable type of wired connector. In other embodiments, the connector is replaced with a wireless connection means. In some embodiments, the mouthpiece incorporates a power source, such as a battery.

Similar to the first embodiment, the mouthpiece 103 also includes electrical circuitry (not shown) feeding a respective series of electrodes 132a, 133a at each surface of each flange 132, 133, that is to say each of the upper and lower surfaces of each of the flanges 132, 133. Each of these electrode series 132a, 133a is electrically isolated from the others by a shielding material, thereby enabling all surrounding muscles to be stimulated simultaneously or in any sequence required. The electrodes 132a, 133a cooperate with the outer surface of the flanges 132, 133 with which they are associated to form a substantially contiguous surface. In this embodiment, the mouthpiece 103 is formed of a silicon grade or a biocompatible grade plastic material. The electrodes 132a, 133a in this embodiment are preferably formed of gold or copper or composite material or any such alloy with an exposed surface.

In use, the mouthpiece 103 is placed in a patient's mouth and the tongue of the patient is received within the mouthpiece 103 such that the dorsal tongue surface 57 is in contact with the first contact flanges 132 and the sublingual tongue surface is in contact with the second contact flanges 133. It will be appreciated by those skilled in the art that the first flanges 132 will contact a rearward portion of the dorsal tongue surface 57 and the second flanges 133 will contact a frontward portion of the sublingual tongue surface. With the patient's mouth closed, the flanges 132, 133 are also able to contact and stimulate adjacent muscles on the other side of the tongue, for example the palate muscles. The muscles are stimulated in a similar manner to the device 1 according to the first embodiment, but this mouthpiece 103 enables the muscles to be stimulated on both sides of the tongue simultaneously. It will be appreciated that with this design, the muscles based in and around the tongue may be stimulated, including those in hard and soft palate areas.

It will be appreciated by those skilled in the art that several variations to the aforementioned embodiments are envisaged without departing from the scope of the invention. For example, the mouthpiece 3 may take any suitable form, but is preferably designed to enable the electrical stimulation to be applied to the appropriate muscles as described above. The dials 24, 25, 26, 27 may be replaced with other similar adjustment means or even omitted as explained above. The mouthpiece 3 and main body 2 may be provided as an integral unit and the charging station 4 may be omitted, for example the main body 2 may incorporate a mains cable 42 or simply require single use batteries or some other power source. Similarly, the USB port 28 may be omitted or replaced with some other connection means, which may be a wireless connection means. It will also be appreciated by those skilled in the art that any number of combinations of the aforementioned features and/or those shown in the appended drawings provide clear advantages over the prior art and are therefore within the scope of the invention described herein.

What is claimed is:

1. A method for training one or more oral muscles of a person by trans mucosal neuromuscular electrical stimulation, the method comprising providing a surface of a tongue with a biphasic electric impulse current during an awake state, to increase resting muscle tone or muscle tone during sleep.

2. A method according to claim 1, the method comprising locating a mouthpiece within the mouth of the person, the mouthpiece comprising a first electrode and a second electrode for contacting the surface of the tongue, and applying said biphasic electric impulse current to the surface of the tongue from the first electrode to the second electrode, to increase resting muscle tone or muscle tone during sleep.

3. A method according to claim 2, wherein the first electrode bears against a dorsal surface of the tongue.

4. A method according to claim 2, wherein the second electrode bears against a dorsal surface of the tongue.

5. A method according to claim 3, wherein the second electrode bears against a sublingual surface of the tongue.

6. A method according to claim 2, wherein the first electrode bears against a sublingual surface of the tongue.

7. A method according to claim 6, wherein the second electrode bears against the sublingual surface of the tongue.

8. A method according to claim 1, wherein said trans mucosal neuromuscular electrical stimulation is provided with a current having a frequency of up to 150 Hz.

9. A method for training one or more oral muscles by trans mucosal neuromuscular electrical stimulation, the method comprising locating a mouthpiece within a mouth of a person, and whilst the person is awake applying electrical stimulation to a sublingual surface of a tongue of the person via the mouthpiece, the trans mucosal neuromuscular electrical stimulation being provided from a first side of the tongue to a second side of the tongue to increase resting muscle tone or muscle tone during sleep.

10. A method according to claim 9, comprising applying the trans mucosal neuromuscular electrical stimulation from the sublingual surface of the tongue, as said first side of the tongue, to a dorsal surface of the tongue, as said second side of the tongue.

11. A method according to claim 9, comprising applying the trans mucosal neuromuscular electrical stimulation to a first lateral portion of the sublingual surface of the tongue, as said first side of the tongue, to a second lateral portion of the sublingual surface of the tongue, as said second side of the tongue.

12. A method according to claim 9, wherein said trans mucosal neuromuscular electrical stimulation is provided with a current having a frequency of up to 150 Hz.

* * * * *